（12）United States Patent
Yeh

(10) Patent No.: US 7,347,823 B2
(45) Date of Patent: Mar. 25, 2008

(54) HEMADYNAMOMETER

(75) Inventor: Chien-Ho Yeh, Taipei (TW)

(73) Assignee: Rossmax International Ltd., Taipei (TW)

( * ) Notice: Subject to any disclaimer, the term of this patent is extended or adjusted under 35 U.S.C. 154(b) by 408 days.

(21) Appl. No.: 10/853,646

(22) Filed: May 26, 2004

(65) Prior Publication Data

US 2005/0075576 A1  Apr. 7, 2005

(30) Foreign Application Priority Data

Oct. 3, 2003  (TW) ............................ 92127522 A

(51) Int. Cl.
*A61B 5/02* (2006.01)
(52) U.S. Cl. .................. 600/500; 600/481; 600/485
(58) Field of Classification Search ............. 600/485, 600/500–503
See application file for complete search history.

(56) References Cited

U.S. PATENT DOCUMENTS 4,660,566 A * 4/1987 Palti ..................... 600/490
5,183,051 A * 2/1993 Kraidin et al. ........... 600/500
5,265,615 A * 11/1993 Frank et al. ............ 600/485
5,301,675 A * 4/1994 Tomita .................. 600/485
5,316,005 A * 5/1994 Tomita .................. 600/493
5,406,952 A * 4/1995 Barnes et al. ........... 600/485
5,533,511 A * 7/1996 Kaspari et al. .......... 600/485
5,772,600 A * 6/1998 Kahn et al. ............ 600/494
2004/0158162 A1* 8/2004 Narimatsu ............. 600/494
2005/0113703 A1* 5/2005 Farringdon et al. ...... 600/509
2006/0224070 A1* 10/2006 Sharrock et al. ........ 600/500

* cited by examiner

*Primary Examiner*—Charles A. Marmor, II
*Assistant Examiner*—Karen E Toth
(74) *Attorney, Agent, or Firm*—Rabin & Berdo, PC

(57) ABSTRACT

A hemadynamometer is provided. The hemadynamometer includes a bag, an inflation unit, a deflation unit, a piezoelectric device and a processor. The bag is used for wounding on the user's wrist or upper arm. The inflation unit is used for inflating the pressure inside the bag, and the deflation unit is used for deflating the pressure inside the bag. When the blood in the artery of the user oppresses the piezoelectric device, the piezoelectric device outputs a number of pulse piezoelectric signals accordingly. The processor is used for comparing the waveform slope of the pulse piezoelectric signals to determine a systolic blood pressure value and a diastolic blood pressure value.

20 Claims, 5 Drawing Sheets

HEMADYNAMOMETER

This application claims the benefit of Taiwan application Serial No. 092127522, filed Oct. 3, 2003, the subject matter of which is incorporated herein by reference.

BACKGROUND OF THE INVENTION

1. Field of the Invention

The invention relates in general to a hemadynamometer, and more particularly to a hemadynamometer with piezoelectric device to make obvious the changes of the blood pressure wave that corresponds to systolic and diastolic pressure values in order to detect systolic and diastolic blood pressure values.

2. Description of the Related Art

Hemadynamometer becomes an indispensable part of modern people's life as people pay more attention on their health. Hemadynamometers on the market nowadays can be categorized into half-automatic hemadynamometers, automatic hemadynamometers, and auscultation hemadynamometers. An auscultation hemadynamometer includes an air bag, a manual pump, an air exhaust valve, a mercury column, and a stethoscope. The medical workers usually use auscultation hemadynamometers which are usually more precise. When using auscultation hemadynamometer, the medical worker winds the upper arm of the user with the air bag, and inflates the air bag using the pump. The medical workers can read the pressure value from the mercury column. The bag pressurizes the artery of the upper arm and temporarily screens off the blood current going through the upper arm. Consequently, the doctor opens the air drain valve to gradually deflate the pressure inside the bag. When the pressure is smaller than the systolic pressure, blood spurts into the region of the bag and then form a swirl. Therefore, the Korotkov's-sound is created. At this moment, the doctor can detect this Korotkov's-sound by the stethoscope, and the pressure inside the air bag is defined as a systolic pressure. The pressure in the air bag continues to deflate; the Korotkov's-sound can still be heard. Upon the moment that the Korotkov's-sound disappears, the pressure inside the air bag is defined as a diastolic pressure. The entire operation is done manually; it takes a long time and is inconvenient. It is also more difficult for the public to judge the correct systolic and diastolic pressures.

Furthermore, users can also use an automatic blood pressure monitor (for example, an oscillation blood pressure monitor) to find out the systolic and diastolic pressures. Firstly, the oscillating blood pressure monitor is used to find out the maximum amplitude ($A_{max}$). Secondly, finding the value of $0.5*A_{max}$ (the value 0.5 is obtained by statistics for example), and treat pressure that corresponds to the value of $0.5 A_{max}$ as the systolic pressure. Then, the value of $0.8 A_{max}$ (the value 0.8 is also obtained by statistics for example) is found out, and the pressure corresponding to the value of $0.8 A_{max}$ is defined as the diastolic pressure. But it is very difficult to distinguish the $A_{max}$ from other neighboring values. If the $A_{max}$ is incorrect, both the systolic and the diastolic pressures are incorrect.

Furthermore, the Korotkov's-sound-based hemadynamometer compares the magnitude of the pulse wave to the baseline (for example 0.5V). If the magnitude of the pulse wave is greater than 0.5V, a beep sound is created. The pressure inside the air bag corresponding to the appearance of first beep sound is defined as the systolic pressure. Then, the pressure inside the air bag corresponding to the disappearance of beep sound is defined as the diastolic pressure. However, the strength of heart pump of every individual is different and therefore, the magnitude of the pulse wave of every individual is also different. If the same baseline (for example, 0.5 and/or 0.8) is used for every one, erroneous pressure values are found.

SUMMARY OF THE INVENTION

It is therefore an object of the invention to provide a hemadynamometer that uses the design of striking the piezoelectric device by blood to create obvious changes of the blood pressure wave. It becomes easier to find the diastolic and systolic pressure values and greatly enhance the accuracy of the measurement.

The invention achieves the above-identified objects by providing a hemadynamometer that is used to measure the blood pressure of the user. The hemadynamometer includes at least a piezoelectric device, a processor and a display unit. When the blood of the artery of the user oppresses the piezoelectric device, the piezoelectric device outputs a number of pulse piezoelectric signals accordingly. The processor is used for comparing the waveform slope of the pulse piezoelectric signals to determine a systolic blood pressure wave and a diastolic blood pressure wave. Then, the processor determined and outputs a systolic blood pressure value and a diastolic blood pressure value corresponding to the systolic and diastolic blood pressure waves respectively. The display unit is used for displaying the systolic and diastolic blood pressure values.

The invention achieves another of the above-identified objects by providing a hemadynamometer that includes a bag, an inflation unit, a deflation unit, a piezoelectric device, a processor and a display unit. The bag is used for wounding on a user's wrist or upper arm. The inflation unit is used for inflating the pressure inside the bag, and the deflation unit is used for deflating the pressure inside the bag. When the blood of the artery of the user oppresses the piezoelectric device, the piezoelectric device outputs a number of pulse piezoelectric signals. The processor is used for comparing the rising rate and the descending rate of the pulse piezoelectric signals to determine a systolic blood pressure wave and a diastolic blood pressure wave. Then, the processor determines and outputs a systolic blood pressure value and a diastolic blood pressure value corresponding to the systolic and diastolic blood pressure waves respectively. The display unit is used for displaying the diastolic blood pressure value and systolic blood pressure value.

The invention achieves another of the above-identified objects by providing a method of blood pressure measuring. First, a bag wound on a user's wrist or upper arm is inflated or deflated. Then, a number of pulse piezoelectric signals are detected during the inflation or deflation step. Finally, the waveform slope of the pulse piezoelectric signals are compared and a systolic blood pressure value and a diastolic blood pressure value are determined.

Other objects, features, and advantages of the invention will become apparent from the following detailed description of the preferred but non-limiting embodiments. The following description is made with reference to the accompanying drawings.

DETAILED DESCRIPTION OF THE INVENTION

Figure 1:
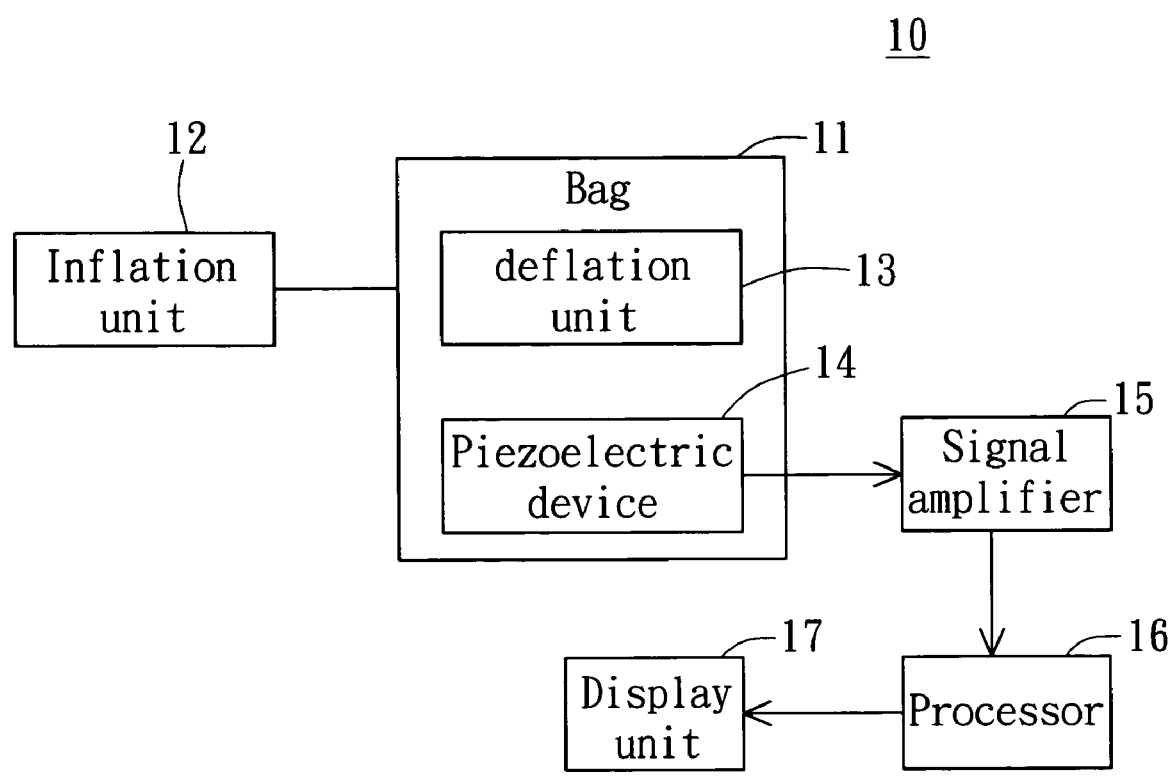
FIG. 1 is the diagram of the preferred embodiment of the hemadynamometer according to the invention.

Please refer to FIG. 1 which is a diagram of a preferred embodiment of hemadynamometer according to the invention. In FIG. 1, the hemadynamometer 10 includes at least a bag 11, an inflation unit 12, a deflation unit 13, a piezoelectric device 14, a signal amplifier 15, a processor 16, and a display unit 17. The bag 11 is used to wind on the user's upper arm or wrist. The inflation unit 12 can pump air into the bag 11 in order to inflate the pressure inside the bag 11. The deflation unit 13 is used to reduce the pressure inside the bag 11.

Before blood pressure measurement, the bag 11 is wound on the user's wrist or upper arm. The inflation unit 12 is used to inflate the pressure inside the bag 11. When the pressure inside the bag 11 is greater than the predefined value (e.g. 220 mmHg) related to the user's systolic pressure (e.g. 140 mmHg), the bag presses on the artery in the upper arm or wrist and temporally stops the blood flow.

Figure 2:
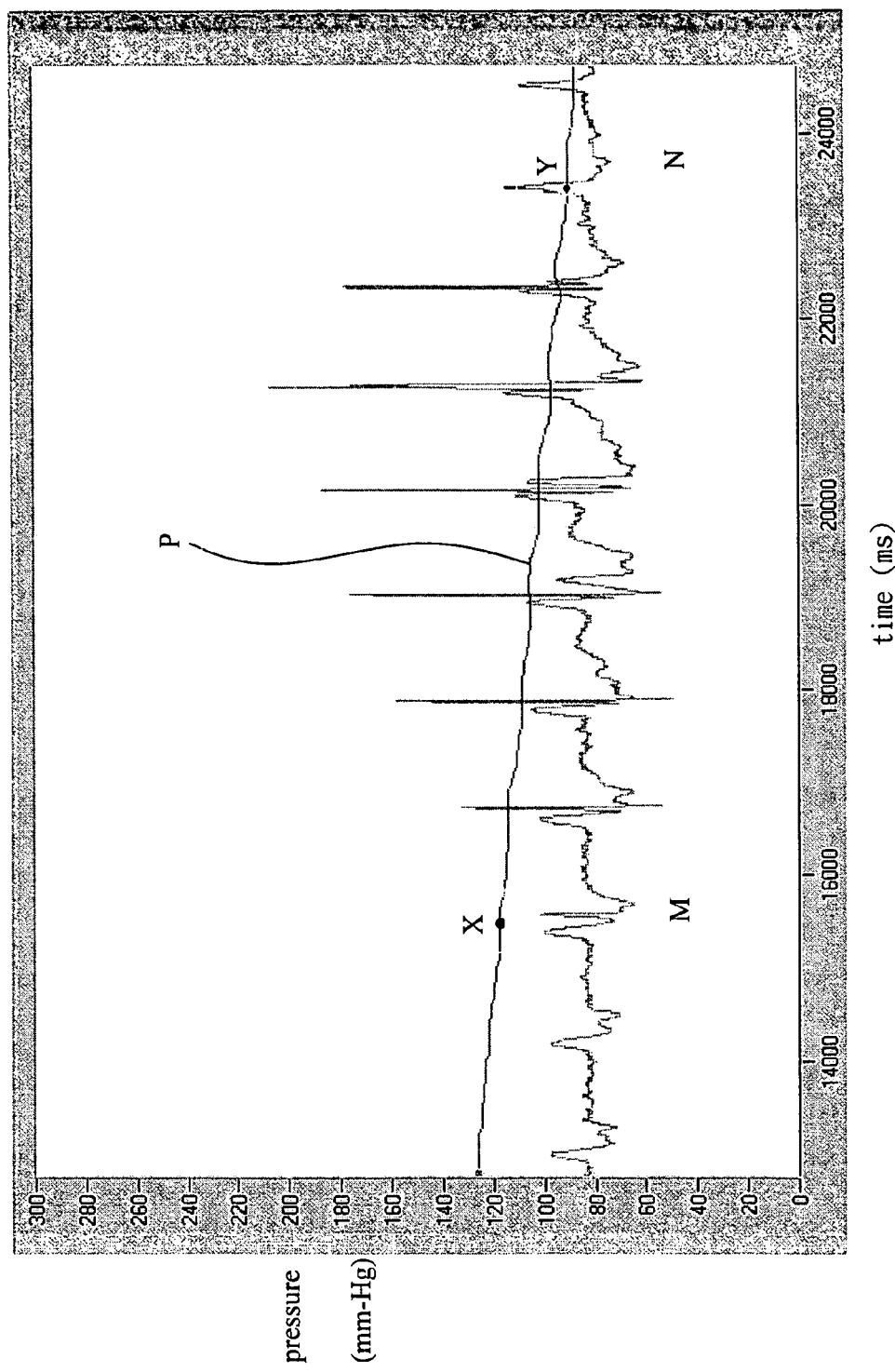
FIG. 2 is the diagram of wave changes when the piezoelectric device in FIG. 1 is stoke by the blood.
Figure 3:
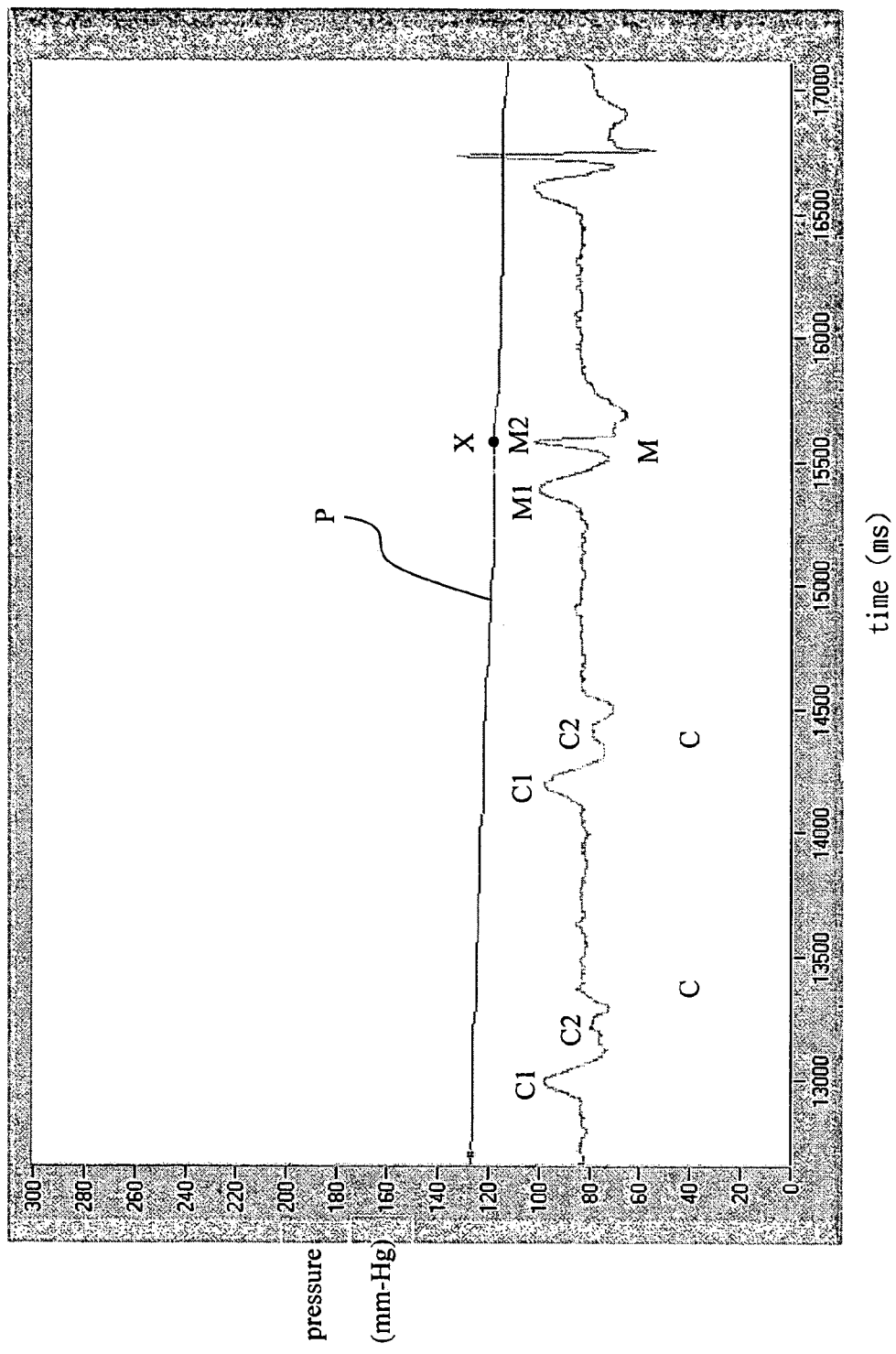
FIG. 3 is the enlarged diagram of the pulse piezoelectric signal nearby the systolic blood pressure wave of FIG. 2.
Figure 4:
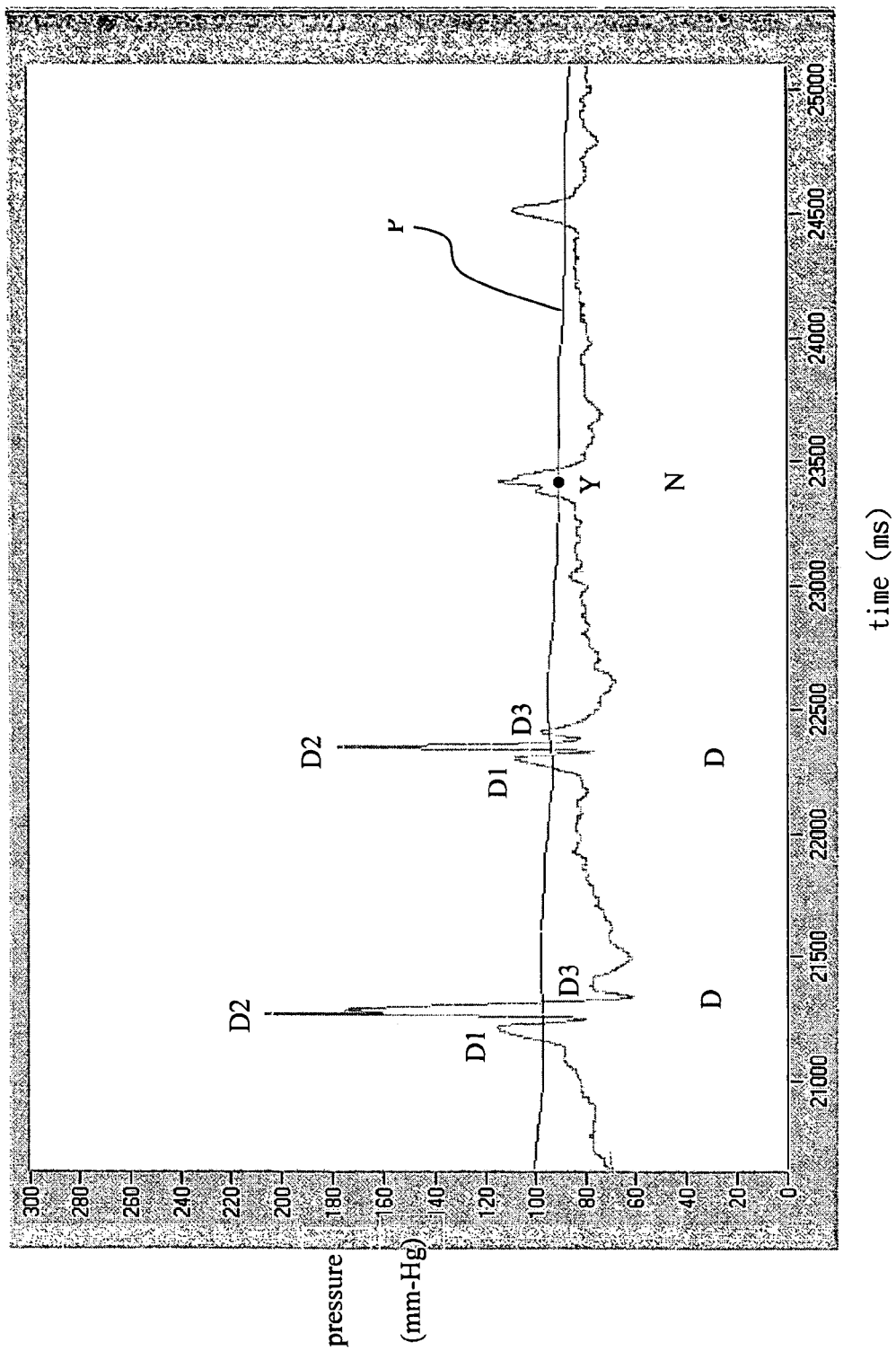
FIG. 4 is the enlarged diagram of the pulse piezoelectric signal nearby the diastolic blood pressure wave of FIG. 2.

Following on, the deflation unit 13 is used to deflate the pressure inside the bag 11. During the process of deflating the pressure, the piezoelectric device 14 inside the bag outputs several pulse piezoelectric signal due to the hit by the blood in the artery. The signal amplifier 15 is electrically connected to the piezoelectric device 14 and can amplify and output the pulse piezoelectric signal. The relationship of the pulse piezoelectric signal and the pressure inside the bag 11 is shown in FIGS. 2-4. The processor 16 is electrically connected to the signal amplifier 15 and is used to compare the waveform slope of the amplified pulse piezoelectric signals to determine a systolic blood pressure wave M and a diastolic blood pressure wave N. Then, the processor 16 determines and outputs the corresponding pressures of the systolic and diastolic blood pressure waves M and N, and defines as a systolic blood pressure value X and a diastolic blood pressure value Y. The display unit 17 is electrically connected to the processor 16 and is used to display the systolic blood pressure value X and the diastolic blood pressure value Y.

In FIG. 2, the horizontal axis represents time and the vertical axis represents the pressure inside the bag 11. When the pressure inside the bag deflates, a pressure curve P is formed. As shown in FIG. 3, every pulse piezoelectric signal C before the systolic blood pressure wave M includes a first wave C1 and a first subsequent wave C2. The systolic blood pressure wave M includes a second wave M1 and a second subsequent wave M2. The rising rate and descending rate of the first subsequent wave C2 are smaller than the rising rate and descending rate of the first wave C1 respectively. The rising rate and descending rate of the second subsequent wave M2 are greater than the rising rate and descending rate of the second wave M1 respectively.

During the measurement, the bag 11 is winded on the user's wrist or upper arm. The user uses the inflation unit 12 to inflate the pressure inside the bag 11 by pumping air into the bag 11. Then, the user can read the pressure value of the bag 11 by convention mercury column or pressure sensing unit. The bag 11 presses on the artery in the wrist or upper arm and temporally stops the blood current. Then the user turns on the deflation unit 13 to gradually reduce the pressure inside the bag 11. When the pressure inside the bag 11 is slightly smaller than the systolic pressure in the artery, the blood in the artery spurts into the region bounded by the bag and forms a swirl. At the same time, blood strikes the piezoelectric device 14 creating systolic blood pressure wave M which occurs simultaneously with the traditional Korotkov's-sound. It is therefore very precise.

The processor 16 determines the first one of the pulse piezoelectric signals whose back wave has a larger rising rate and descending rate greater than the rising rate and the descending rate of the front wave as the systolic blood pressure wave M corresponding to the systolic blood pressure value X.

As shown in FIG. 4, the rising rate and the descending rate of the diastolic blood pressure wave N are respectively smaller than the rising rate and the descending rate of the second subsequent wave M2 of the systolic blood pressure wave M. Therefore, the processor 16 determines the first one of the pulse piezoelectric signals having a smaller rising rate and descending rate than the rising rate and the descending rate of the second subsequent wave M2 of the systolic blood pressure wave M as the diastolic blood pressure wave N corresponding diastolic blood pressure value Y.

Alternatively, each of the pulse piezoelectric signals D between the diastolic blood pressure wave N and the systolic blood pressure wave M includes a third front wave D1, a middle wave D2, and a third back wave D3 corresponding to the continuous Korotkov's-sound in the traditional method. The rising rate and the descending rate of the middle wave D2 are respectively greater than the rising rate and the descending rate of the third front wave D1 and the third back wave D3. The rising rate and the descending rate of the diastolic pressure wave N are respectively smaller than the rising rate and the descending rate of the middle wave D2 adjacent to the diastolic blood pressure wave N. The moment that the diastolic blood pressure wave N appears is the same moment as the Korotkov's-sound disappear in the traditional method.

Figure 5:
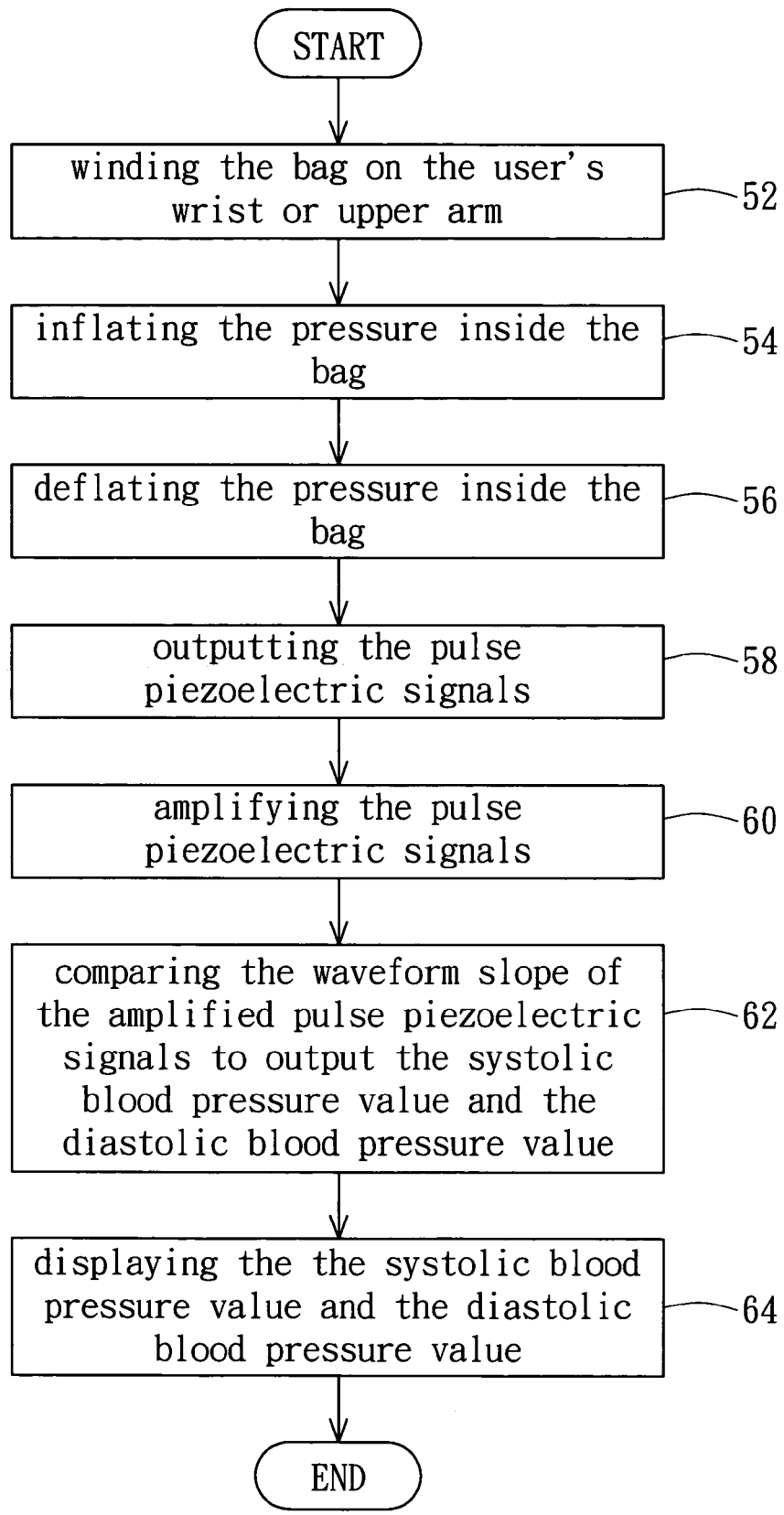
FIG. 5 is a flowchart of a preferred embodiment of the method of measuring blood pressure according to the invention.

Please refer to FIG. 5, which is a flowchart of a preferred embodiment of the method of measuring blood pressure according to the invention. Firstly, in step 52, the bag 11 is winded on the wrist or upper arm of the user. Then, the inflation unit 12 is used to inflate the pressure inside the bag 11 to a predefined value (e.g. 220 mmHg) that is greater than the ordinary systolic pressure (e.g. 140 mmHg) as shown in step 54. The deflation unit 13 is then used to deflate the pressure inside the bag 11 as shown in step 56. The piezoelectric device 14 inside the bag outputs a number of pulse piezoelectric signals according to the strikes of the blood in the artery as shown in step 58.

The signal amplifier 15 amplifies the wave of the pulse piezoelectric signals as shown in step 60. The processor 16 compares the waveform slope of the amplified piezoelectric signals to determine a systolic blood pressure wave M and a diastolic blood pressure wave N. Then, the processor determines and outputs a systolic blood pressure value and a diastolic blood pressure value wherein the method of determining the waveform slope had been mentioned previously and is not repeated here. The display unit 17 is used to display the systolic and the diastolic blood pressure values as shown in step 64.

However, for those who understand the invention know that the technologies used in this invention can varies; for example, the processor 16 can be a microprocessor, and the display unit 18 can either be a liquid crystal display or an organic light emitting diode (OLED) display. Furthermore, the inflation unit 12 includes at least one of a automatic and a manual pump, and the deflation unit 13 includes an air exhaust valve. Furthermore, the hemadynamometer 10 can also includes a pressure sensing unit for sensing the pressure inside the bag 11 and outputting the blood pressure value.

The hemadynamometer disclosed in the above embodiment utilizes the design of blood striking the piezoelectric device to create obvious changes of the blood pressure wave. It becomes easier to find the diastolic and systolic pressure values and greatly enhance the accuracy of the measurement.

Furthermore, measuring the blood pressure during the deflation step is used to explain the invention, but blood pressure can also be measured during inflation step according to the invention.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A hemadynamometer, comprising:
   a piezoelectric device for being pressed by the blood in the artery of a user to output a plurality of pulse piezoelectric signals accordingly;
   a processor for comparing the waveform slope of the pulse piezoelectric signals to determine a systolic blood pressure wave and a diastolic blood pressure wave, wherein the processor determines and outputs a systolic blood pressure value and a diastolic blood pressure value corresponding to the systolic and diastolic blood pressure waves, respectively, wherein each of the pulse piezoelectric signals before the systolic blood pressure wave has a first wave and a second wave, and the systolic blood pressure wave has a first wave and a second wave, wherein a rising rate and a descending rate of the second wave of the pulse piezoelectric signal are smaller than a rising rate and a descending rate of the first wave of the pulse piezoelectric signal, respectively, a rising rate and a descending rate of the second wave of the systolic blood pressure wave being greater than a rising rate and a descending rate of the first wave of the systolic blood pressure wave, respectively; and
   a display unit for displaying the systolic and diastolic blood pressure values.

2. The hemadynamometer according to claim 1, wherein the processor determines the first one of the pulse piezoelectric signals whose second wave has a larger rising rate and descending rate than the rising rate and the descending rate of the first wave as the systolic blood pressure wave corresponding to the systolic blood pressure value.

3. The hemadynamometer according to claim 1, wherein the rising rate and the descending rate of the diastolic blood pressure wave are smaller than the rising rate and the descending rate of the second wave of the systolic blood pressure wave respectively.

4. The hemadynamometer according to claim 3, wherein the processor determines the first one of the pulse piezoelectric signals having a smaller rising rate and a descending rate than the rising rate and the descending rate of the second wave of the systolic blood pressure wave as the diastolic blood pressure wave corresponding to the diastolic blood pressure value.

5. The hemadynamometer according to claim 1, wherein at least one of the pulse piezoelectric signals between the systolic blood pressure wave and the diastolic blood pressure wave has a first wave, a second wave subsequent to the first wave, and a third wave subsequent to the second wave, wherein a rising rate and a descending rate of the second wave are greater than a rising rate and a descending rate of the first wave and the third wave respectively, and a rising rate and a descending rate of the diastolic blood pressure wave are respectively smaller than a rising rate and a descending rate of the second wave of the pulse piezoelectric signal adjacent to the diastolic blood pressure wave.

6. The hemadynamometer according to claim 1, wherein the hemadynamometer further comprises:
   a bag for winding on the user's wrist or upper arm;
   an inflation unit for inflating the pressure inside the bag;
   a deflation unit for deflating the pressure inside the bag; and
   a pressure sensing unit for sensing the pressure inside the bag to output a pressure value.

7. The hemadynamometer according to claim 6, wherein the inflation unit comprises at least one of a motor and a manual pump, and the deflation unit comprises an air exhaust valve.

8. A hemadynamometer comprising:
   a bag for winding on a user's wrist or upper arm;
   an inflation unit for inflating the pressure inside the bag;
   a deflation unit for deflating the pressure inside the bag;
   a piezoelectric device for being pressed by blood in the artery of a user to output a plurality of pulse piezoelectric signals accordingly;
   a processor for comparing the waveform slope of the pulse piezoelectric signals to determine a systolic blood pressure wave and a diastolic blood pressure wave, wherein the processor outputs a systolic blood pressure value and a diastolic blood pressure value according the systolic and diastolic blood pressure waves, respectively, wherein each of the pulse piezoelectric signals before the systolic blood pressure wave has a first wave and a second wave, and the systolic blood pressure wave has a first wave and a second wave, wherein a rising rate and a descending rate of the second wave of the pulse piezoelectric signal are smaller than a rising rate and a descending rate of the first wave of the pulse piezoelectric signal respectively, a rising rate and a descending rate of the second wave of the systolic blood pressure wave being greater than a rising rate and a descending rate of the first wave of the systolic blood pressure wave, respectively; and
   a display unit for displaying the systolic and diastolic blood pressure values.

9. The hemadynamometer according to claim 8, wherein the processor determines the first one of the pulse piezoelectric signals whose second wave has a larger rising rate and descending rate than the rising rate and the descending rate of the first wave as the systolic blood pressure wave corresponding to the systolic blood pressure value.

10. The hemadynamometer according to claim 8, wherein the rising rate and the descending rate of the diastolic blood pressure wave are smaller than the rising rate and the descending rate of the second wave of the systolic blood pressure wave respectively.

11. The hemadynamometer according to claim 10, wherein the processor determines the first one of the pulse piezoelectric signals having a smaller rising rate and a descending rate than the rising rate and the descending rate of the second wave of the systolic blood pressure wave as the diastolic blood pressure wave corresponding to the diastolic blood pressure value.

12. The hemadynamometer according to claim 8, wherein at least one of the pulse piezoelectric signals between the systolic blood pressure wave and the diastolic blood pressure wave has a first wave, a second wave subsequent to the first wave, and a third wave subsequent to the second wave, wherein a rising rate and a descending rate of the second wave are greater than a rising rate and a descending rate of the first wave and the third wave respectively, and a rising rate and a descending rate of the diastolic blood pressure wave are respectively smaller than a rising rate and a descending rate of the second wave of the pulse piezoelectric signal adjacent to the diastolic blood pressure wave.

13. The hemadynamometer according to claim 8, wherein the hemadynamometer further comprises:
   a pressure sensing unit for sensing the pressure inside the bag to output a pressure value.

14. The hemadynamometer according to claim 8, wherein the inflation unit comprises at least one of a motor and a manual pump, and the deflation unit comprises an air exhaust valve.

15. A method for measuring the blood pressure, comprising:
   inflating or deflating the pressure inside a bag wound on a user's wrist or upper arm;
   detecting a plurality of Pulse piezoelectric signals during the inflation or deflation step, wherein each of the pulse piezoelectric signals before the systolic blood pressure wave has a first wave and a second wave, and the systolic blood pressure wave has a first wave and a second wave, wherein a rising rate and a descending rate of the second wave of the pulse piezoelectric signal are smaller than a rising rate and a descending rate of the first wave of the pulse piezoelectric signal, respectively, a rising rate and a descending rate of the second wave of the systolic blood pressure wave being greater than a rising rate and a descending rate of the first wave of the systolic blood pressure wave, respectively; and
   comparing the waveform slope of the pulse piezoelectric signals to determine a systolic blood pressure value and a diastolic blood pressure value, wherein the comparing step comprises:
      amplifying the pulse piezoelectric signals; and
      comparing the waveform slope of the amplified pulse piezoelectric signals to determine a systolic blood pressure wave and a diastolic blood pressure wave, and then outputting the systolic blood pressure value and the diastolic blood pressure value based on the systolic blood pressure wave and the diastolic blood pressure wave.

16. The method according to claim 15, wherein the step of determining a systolic blood pressure wave further comprises:
   determining the first one of the pulse piezoelectric signal whose second wave has a larger rising rate and descending rate greater than the rising rate and the descending rate of the first wave as the systolic blood pressure wave corresponding to the systolic blood pressure value.

17. The method according to claim 15, wherein the rising rate and the descending rate of the diastolic blood pressure wave are smaller than the rising rate and the descending rate of the second wave of the systolic blood pressure wave respectively.

18. The method according to claim 17, wherein the step of determining a diastolic blood pressure wave further comprises:
   determining the first one of the pulse piezoelectric signals having a smaller rising rate and descending rate than the rising rate and the descending rate of the second wave of the systolic pressure wave as the diastolic blood pressure wave corresponding to the diastolic blood pressure value.

19. The method according to claim 15, further comprising:
   sensing the pressure inside the bag to output a pressure value.

20. The method according to claim 15, further comprising:
   displaying the systolic and diastolic blood pressure values.

* * * * *